United States Patent
Johnson et al.

(10) Patent No.: US 10,342,443 B2
(45) Date of Patent: *Jul. 9, 2019

(54) SYSTEM, METHOD, APPARATUS, DEVICE AND COMPUTER PROGRAM PRODUCT FOR AUTOMATICALLY DETECTING POSITIONING EFFECT

(71) Applicant: SafeOp Surgical, Inc., Hunt Valley, MD (US)

(72) Inventors: Samuel Johnson, Harrisburg, PA (US); Richard A O'Brien, Westminster, MD (US)

(73) Assignee: SafeOp Surgical, Inc., Hunt Valley, MD (US)

( * ) Notice: Subject to any disclaimer, the term of this patent is extended or adjusted under 35 U.S.C. 154(b) by 453 days.

This patent is subject to a terminal disclaimer.

(21) Appl. No.: 14/968,544

(22) Filed: Dec. 14, 2015

(65) Prior Publication Data

US 2016/0095525 A1    Apr. 7, 2016

Related U.S. Application Data

(62) Division of application No. 12/620,384, filed on Nov. 17, 2009, now Pat. No. 9,211,074.

(Continued)

(51) Int. Cl.
*A61B 5/00* (2006.01)
*A61B 5/04* (2006.01)
(Continued)

(52) U.S. Cl.
CPC ........ *A61B 5/04001* (2013.01); *A61B 5/4041* (2013.01); *A61B 5/4821* (2013.01);
(Continued)

(58) Field of Classification Search
CPC . A61B 5/04001; A61B 5/4041; A61B 5/4821; A61B 5/4893; A61B 5/742;
(Continued)

(56) References Cited

U.S. PATENT DOCUMENTS 5,313,956 A    5/1994   Knutsson et al.
5,916,179 A    6/1999   Sharrock
(Continued)

FOREIGN PATENT DOCUMENTS

CN    101137332      3/2008
CN    201185940 Y    1/2009
(Continued)

OTHER PUBLICATIONS

"NeuroStream—Customizable IOM Software" [online][retrieved Apr. 21, 2010]. Retrieved from the Internet at http://www.neurostream.us/features_benefits_adaptsToYou.jsp?nav=3.

(Continued)

*Primary Examiner* — Devin B Henson
(74) *Attorney, Agent, or Firm* — Mintz Levin Cohn Ferris Glovsky and Popeo, P.C.

(57) ABSTRACT

An automated system, method, apparatus, device and/or computer program product for detecting positioning effect is set forth, the apparatus according to an exemplary embodiment may include an output operable to couple to one or more stimulating electrodes to stimulate one or more peripheral nerves of the patient, an input operable to couple to one or more recording electrodes to record resultant electrical waveforms generated by a nervous system of a patient in response to the stimulating module, and one or more processors operable to identify the positioning effect based on the resultant electrical waveforms.

15 Claims, 3 Drawing Sheets

Related U.S. Application Data

(60) Provisional application No. 61/185,441, filed on Jun. 9, 2009.

(51) Int. Cl.
*A61B 5/11* (2006.01)
*A61G 13/12* (2006.01)
*A61G 13/10* (2006.01)
*A61G 13/00* (2006.01)

(52) U.S. Cl.
CPC .......... *A61B 5/7203* (2013.01); *A61B 5/7275* (2013.01); *A61B 5/742* (2013.01); *A61B 5/746* (2013.01); *A61G 13/10* (2013.01); *A61G 13/12* (2013.01); *A61B 5/04* (2013.01); *A61B 5/1106* (2013.01); *A61B 5/4893* (2013.01); *A61G 13/0036* (2013.01)

(58) Field of Classification Search
CPC ..... A61B 5/7425; A61B 5/746; A61B 5/1106; A61G 13/10; A61G 13/0036
See application file for complete search history.

(56) References Cited

U.S. PATENT DOCUMENTS

| | | | |
|---|---|---|---|
| 6,634,043 B2 | 10/2003 | Lamb et al. | |
| 6,725,086 B2 | 4/2004 | Marinello | |
| 7,234,180 B2 | 6/2007 | Horton et al. | |
| 7,522,953 B2 | 4/2009 | Kaula et al. | |
| 7,806,862 B2 | 10/2010 | Molnar | |
| 8,255,045 B2 | 8/2012 | Gharib et al. | |
| 8,731,654 B2 * | 5/2014 | Johnson | A61B 5/04001 600/382 |
| 9,211,074 B2 * | 12/2015 | Johnson | A61B 5/04001 |
| 2003/0176799 A1 | 9/2003 | Beatty et al. | |
| 2005/0075578 A1 | 4/2005 | Gharib et al. | |
| 2007/0192960 A1 | 8/2007 | Jackson | |
| 2007/0282217 A1 | 12/2007 | McGinnis et al. | |
| 2008/0167574 A1 | 7/2008 | Farquhar | |
| 2008/0221473 A1 | 9/2008 | Calancie et al. | |
| 2008/0300655 A1 | 12/2008 | Cholette | |
| 2009/0033486 A1 | 2/2009 | Costantino | |
| 2009/0177112 A1 | 7/2009 | Gharib et al. | |
| 2012/0095360 A1 * | 4/2012 | Runney | A61B 5/0484 600/546 |

FOREIGN PATENT DOCUMENTS

| | | |
|---|---|---|
| JP | H1176185 A | 3/1999 |
| JP | 2004-517669 | 6/2004 |
| JP | 2009-534159 | 9/2009 |
| WO | WO-2006/072050 A2 | 7/2006 |
| WO | WO-2006/084193 A2 | 8/2006 |

OTHER PUBLICATIONS

"NeuroStream—Intraoperative Monitoring Document Management" [online][retrieved Apr. 21, 2010]. Retrieved from the Internet at http://www.neurostream.us/solutions_onlineDoc.jsp?nav=1.
"NeuroStream—Intraoperative Monitoring Interpreting Physician Access" [online][retrieved Apr. 21, 2010]. Retrieved from the Internet at http://www.neurostream.us/solutions_telemedicine.jsp?nav=1.
"NeuroStream—IOM Administrative Efficiency Software" [online][retrieved Apr. 21, 2010]. Retrieved from the Internet at ttp://www.neurostream.us/features_benefits_savesTime.jsp?nav=3.
"NeuroStream—IOM and Neurophysiological Monitoring Business Analysis Software" [online][retrieved Apr. 21, 2010]. Retrieved from the Internet at http://www.neurostream.us/solutions_reports.jsp?nav=1.
"NeuroStream—IOM and Neurophysiological Monitoring Software Support" [online][retrieved Apr. 21, 2010]. Retrieved from the Internet at http://www.neurostream.us/features_benefits_support.jsp?nav=3.
"NeuroStream—IOM and Neurophysiological Monitoring Software" [online][retrieved Apr. 21, 2010]. Retrieved from the Internet at http://www.neurostream.us/solutions_caseExecution.jsp?nav=1.
"NeuroStream—IOM Office Automation Software" [online][retrieved Apr. 21, 2010]. Retrieved from the Internet at http://www.neurostream.us/features_benefits_totalWorkflow.jsp?nav=3.
"NeuroStream—IOM Software as a Service Security" [online][retrieved Apr. 21, 2010]. Retrieved from the Internet at http://www.neurostream.us/features_benefits_secure.jsp?nav=3.
"NeuroStream—IOM Web-Based Software as a Service (SaaS)" [online][retrieved Apr. 21, 2010]. Retrieved from the Internet at http://www.neurostream.us/features_benefits_accessAnywhere.jsp?nav=3.
"NeuroStream—Learning IOM Administrative Software" [online][retrieved Apr. 21, 2010]. Retrieved from the Internet at http://www.neurostream.us/features_benefits_easyToLearn.jsp?nav=3.
"NeuroStream—Intraoperative Monitoring Medical Billing Software" [online][retrieved Apr. 21, 2010]. Retrieved from the Internet at http://www.neurostream.us/solutions_billing.jsp?nav=1.
"NeuroStream—Software for Intraoperative Monitoring Scheduling" [online][retrieved Apr. 21, 2010]. Retrieved from the Internet at http://www.neurostream.us/solutions_scheduling.jsp?nav=1.
AMSCO 3085 SP Surgical Table Sales Brochure, Steris Corporation; Apr. 2006, 16 pages.
Baumann, et al., Intraoperative SSEP Detection of Ulnar Nerve Compression or Ischemia in an Obese Patient: A Unique Complication Associated With a Specialized Spinal Retraction System; Archives of Physical Medicine and Rehabilitation, vol. 81, No. 1 Jan. 2000, 3 pages.
Ben-David, et al., Prognosis of Intraoperative Brachial Plexus Injury: A Review of 22 cases, British Journal of Anaesthesia, vol. 79, No. 4, Oct. 1997, pp. 440-445.
Bizzarri, et al., Iatrogenic Injury to the Long Thoracic Nerve: An Underestimated Cause of Morbidity After Cardiac Surgery, Texas Heart Institute Journal, vol. 28, No. 4, Jan. 2001, pp. 315-317.
Chinese Office Action for Application No. 201080025776.9, dated Jan. 21, 2014, 8 pages.
European Office Action Application No. 10786543.8, dated Feb. 19, 2014, 4 pages.
European Office Action for Application No. 10786543.8, dated Jan. 5, 2016, 4 pages.
European Office Action for Application No. 10786543.8, dated Mar. 31, 2015, 5 pages.
European Office Action for Application No. 10786543.8, dated Sep. 24, 2014, 5 pages.
Fishel, et al., Case Report: Postoperative Injuries of Upper Limb Nerves, The Clinical Journal of Pain, vol. 6, No. 2, Jun. 1990, pp. 128-130.
Graham, et al., Brachial Plexus Injury After Median Sternotomy, Journal of Neurology, Neurosurgery, and Psychiatry, vol. 44, Jul. 1981, pp. 621-625.
Hickey, et al., "Intraoperative Somatosensory Evoked Potential Monitoring Predicts Peripheral Nerve Injury During Cardiac Surgery," Anesthesiology, vol. 78, No. 1, Jan. 1993, pp. 29-35.
International Search Report and Written Opinion for PCT Application No. PCT/US2010/034076, dated Jul. 9, 2010, 8 pages.
Japanese Office action for Application No. 2012-514965 with English Translation, dated Apr. 8, 2014, 6 pages.
Japanese Office Action for Application No. 2012-514965, dated Feb. 3, 2015, 4 pages.
Jellish, et al. Hands-Up Positioning During Asymmetric Sternal Retraction for Internal Mammary Artery Harvest: A Possible Method to Reduce Brachial Plexus Injury, Anesthesia and Analgesia, vol. 84, No. 2, Feb. 1997, pp. 260-265.
Kamel, et al., "The Use of Sematosensory Evoked Potentials to Determine the Relationship Between Patient Positioning and Impending Upper Extremity Nerve Injury During Spine Surgery: A Retrospective Analysis", Anesth Anala 102(5), May 2006, 1538-1542.

(56) References Cited

OTHER PUBLICATIONS

Labrom, et al., Clinical Usefulness of Somatosensory Evoked Potentials for Detection of Brachial Plexopathy Secondary to Malpositioning in Scoliosis Surgery, Spine 30(18), Sep. 2005, 2089-2093.

Makarov, et al., Intraoperative SSEP Monitoring During External Fixation Procedures in the Lower Extremities, Journal of Pediatric Orthopaedics, vol. 16, No. 2, Mar./Apr. 1996, pp. 155-160.

Makarov, et al., Monitoring Peripheral Nerve Function During External Fixation of Upper Extremities, Journal of Pediatric Orthopaedics, vol. 17, No. 5, Sep./Oct. 1997, pp. 663-667.

Nagda, et al., Neer Award 2005: Peripheral Nerve Function During Shoulder Arthoplasty Using Intraoperative Nerve Monitoring, Journal of Shoulder and Elbow Surgery, vol. 16, No. 3, Supplement, May-Jun. 2007, 7 pages.

Posta, Jr., et al., Neurologic Injury in the Upper Extremity After Total Hip Arthroplasty, Clinical Orthopaedics and Related Research, vol. 345, Dec. 1997, pp. 181-186.

Prielipp, et al., Ulnar Nerve Pressure: Influence of Arm Position and Relationship to Somatosensory Evoked Potentials, Anesthesiology, vol. 91, No. 2, Aug. 1999, 10 pages.

State International Search Report Office of P.R.C. dated Aug. 2, 2013 for Chinese Patent Application No. 201080025776.9, 2 pages.

Supplemental European Search Report for European Patent Application No. 10786543.8, dated Oct. 30, 2013, 5 pages.

U.S. Notice of Allowance for U.S. Appl. No. 12/620,384, dated Aug. 10, 2015, 9 pages.

U.S. Notice of Allowance for U.S. Appl. No. 13/364,444, dated Mar. 19, 2014, 8 pages.

U.S. Office Action for U.S. Appl. No. 12/620,384, dated Dec. 18, 2013, 13 pages.

U.S. Office Action for U.S. Appl. No. 12/620,384, dated Jul. 16, 2014, 16 pages.

U.S. Office Action for U.S. Appl. No. 13/364,444, dated Apr. 25, 2013, 11 pages.

U.S. Office Action for U.S. Appl. No. 13/364,444, dated Dec. 19, 2013, 15 pages.

Warner, et al., Ulnar Neuropathy: Incidence, Outcome, and Risk Factors in Sedated or Anesthetized Patients; Anesthesiology, vol. 81, No. 6, Dec. 1994, 9 pages.

Winfree, et al., Intraoperative Positioning Nerve Injuries, Surgical Neurology, vol. 63, No. 1, Jan. 2005, pp. 5-18.

\* cited by examiner

SYSTEM, METHOD, APPARATUS, DEVICE AND COMPUTER PROGRAM PRODUCT FOR AUTOMATICALLY DETECTING POSITIONING EFFECT

CROSS-REFERENCE TO RELATED PATENT APPLICATIONS

This application is a divisional of U.S. patent application Ser. No. 12/620,384, filed Nov. 17, 2009, incorporated herein by reference in its entirety, which claims priority from Provisional Application U.S. Application 61/185,441, filed Jun. 9, 2009, incorporated herein by reference in its entirety.

BACKGROUND

The present invention relates to a medical device, and more particularly to a device for injury detection.

During many types of surgeries, patients are positioned, e.g., by medical workers, to facilitate surgical access in ways that may put undue tension or pressure on peripheral nervous structures. This undue tension or pressure can create what is generally termed as a "positioning effect." Warning signs of positioning effect may include sensations, such as, e.g., but not limited to, numbness, tingling or weakness. During surgery, a patient is usually placed under general anesthesia. Therefore, they would be unable to identify the usual warning signs resulting from positioning effect. Consequentially, the patient would be left in this compromised position for the duration of the surgical procedure. Continued trauma from positioning effect may result in prolonged or even permanent injury. An injury caused by positioning effect is known as a "positioning effect injury." What is needed is a method to prevent positioning effect injuries.

SUMMARY OF THE INVENTION

In an exemplary embodiment of the present invention a system, method, device, apparatus, and/or computer program product for automatically detecting positioning effect and avoiding such injuries is disclosed.

According to an exemplary embodiment, a method of identifying positioning effect in a patient may be provided. According to an exemplary embodiment, the method may include stimulating one or more peripheral nerves with one or more electrical pulses from one or more stimulating electrodes, recording resultant electrical waveforms generated by a nervous system of the patient in response to the electrical pulses using one or more recording electrodes, and identifying, by or with one or more computing devices, the positioning effect based on the resultant electrical waveforms.

According to an exemplary embodiment, the one or more stimulating electrodes may be coupled to one or more of an arm of the patient, a leg of the patient, an ulnar nerve of the patient, a median nerve of the patient, or a posterior tibial nerve of the patient.

According to an exemplary embodiment, the one or more recording electrodes may be coupled to one or more of a trunk of the patient, an Erb's point of the patient, a head of the patient or a neck of the patient.

According to an exemplary embodiment, the resultant electrical waveforms may be somatosensory evoked potential waveforms.

According to an exemplary embodiment, The identifying may include one or more of comparing, with the computing device, information based on the resultant electrical waveforms to information from an anesthesia machine to determine when changes in the resultant electrical waveforms are due to anesthesia and/or comparing, with the one or more computing devices, information based on the resultant electrical waveforms to information from, e.g., but not limited to, a blood pressure machine to determine when changes in the resultant electrical waveforms are due to blood pressure.

According to an exemplary embodiment, the method may further include determining how to reduce the positioning effect based on a position of a table.

According to an exemplary embodiment, the method may further include providing information based on the positioning effect to a table.

According to an exemplary embodiment, the method may further include providing information to a table to at least partially reposition the table to reduce the positioning effect.

According to an exemplary embodiment, the method may further include adjusting a position of the patient based on the positioning effect using an electro-mechanism of a table.

According to an exemplary embodiment, the method may further include alerting a user to the positioning effect using one or more of a notification, an alert, a communication, an indication, and/or an alarm.

The method may further include displaying information based on the resultant electrical waveforms on a display unit.

According to an exemplary embodiment, the method may further include receiving a user input regarding the accuracy of the resultant electrical waveforms.

According to an exemplary embodiment, an automated apparatus for detecting positioning effect leading to a potential positioning effect injury may include an output operable to connect and/or couple to one or more stimulating electrodes to stimulate one or more peripheral nerves of a patient, an input operable to connect and/or couple to one or more recording electrodes to record resultant electrical waveforms generated by a nervous system in response to the one or more stimulating electrodes, and one or more processors, connected and/or coupled to the output and the input, operable to identify the positioning effect based on the resultant electrical waveforms.

According to an exemplary embodiment, the processor may further include means for identifying the positioning effect which may include one or more means for identifying changes in a latency of the resultant electrical waveforms, means for identifying changes in an amplitude of the resultant electrical waveforms, and/or means for identifying changes in a morphology of the resultant electrical waveforms.

According to an exemplary embodiment, the apparatus may further include a display unit, connected and/or coupled to the one or more processors, operable to display information regarding the resultant electrical waveforms.

According to an exemplary embodiment, the apparatus may further include an alert unit, coupled to the one or more processors, operable to alert a user to the positioning effect.

According to an exemplary embodiment, the apparatus may further include an interface, connected and/or coupled to the processor, operable to couple a table to the processor.

According to an exemplary embodiment, the interface may be operable to transfer information between the table and the one or more processors to reduce the positioning effect.

According to an exemplary embodiment, the apparatus may further include a table.

According to another exemplary embodiment, the apparatus may further include one or more means for obtaining information from an anesthesia machine to determine when changes in the resultant electrical waveforms are due to anesthesia; an anesthesia machine; means for obtaining information from a blood pressure machine to determine when changes in the resultant electrical waveforms are due to blood pressure; or a blood pressure machine.

Further features and advantages of the invention, as well as the structure and operation of various exemplary embodiments of the invention, are described in detail below with reference to the accompanying drawings.

BRIEF DESCRIPTION OF THE DRAWINGS

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements. The left most digits in the corresponding reference number indicate the drawing in which an element first appears.

DETAILED DESCRIPTION

Figure 1:
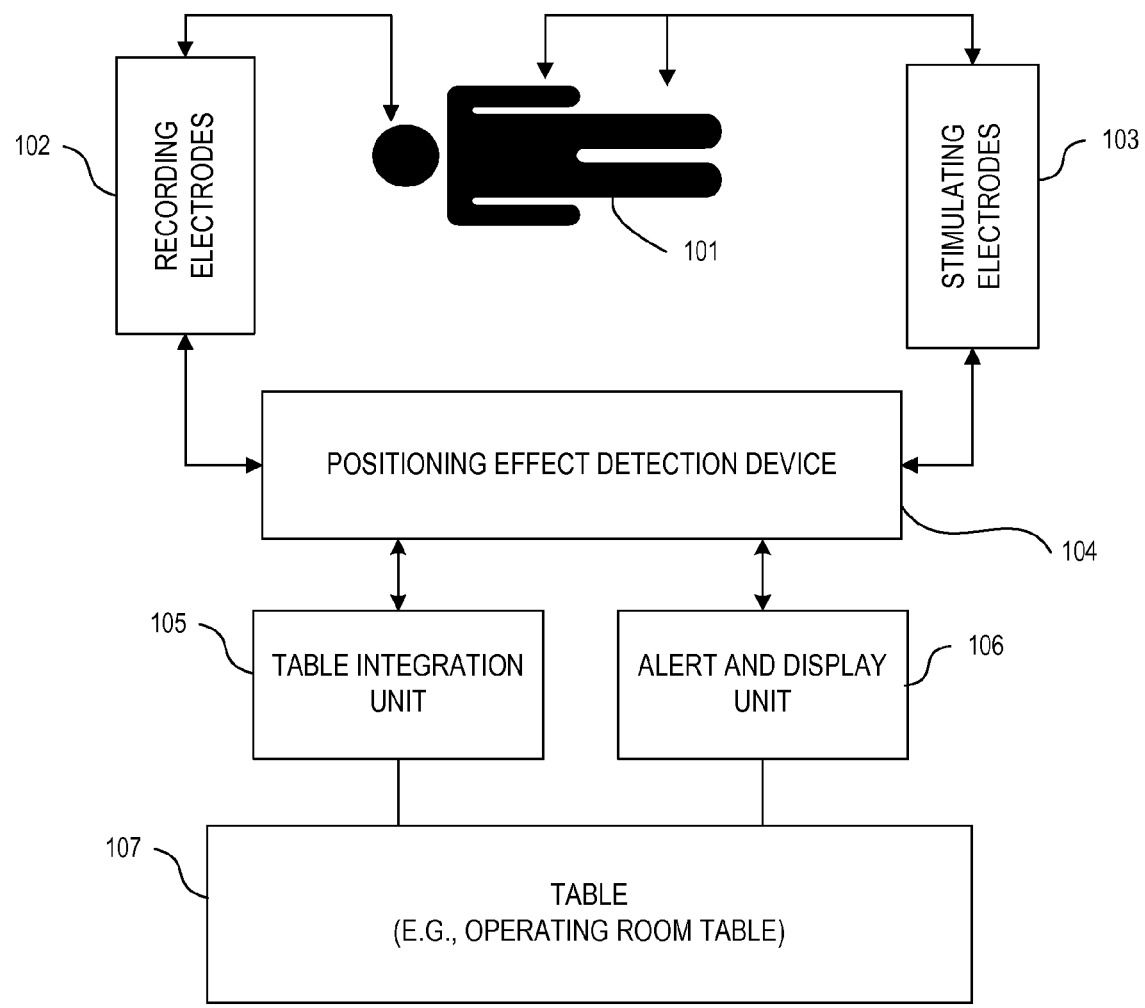
FIG. 1 depicts an exemplary diagram of the system according to an exemplary embodiment of the present invention.

Various exemplary embodiments of the invention including preferred embodiments are discussed in detail below. While specific exemplary embodiments are discussed, it should be understood that this is done for illustration purposes only. A person skilled in the relevant art will recognize that other components and configurations can be used without parting from the spirit and scope of the invention.

The danger of positioning effect injuries is recognized. Despite careful positioning and padding of structures at risk to positioning effect by operating room teams, positioning effect injuries still occur in significant numbers in many surgical types. See, for example, C. J. Winfree and D. G. Kline, "Intraoperative positioning nerve injuries," *Surgical Neurology*, 63(1), pages 5-18, published 2005. Surgical table equipment manufacturers spend considerable time and energy engineering surgical tables attempting to prevent such injuries.

Impending positioning effect injuries can be detected based on somatosensory evoked potentials (SEPs) by specially trained personnel using conventional attended intraoperative neurophysiologic monitoring (IONM) systems. SEPs are summated electrical potentials usually recorded from the head or neck area after repeatedly stimulating a peripheral nerve. Monitoring patients using SEPs during surgery has been shown to allow early identification of impending positioning effect injury that can then be avoided by repositioning the patient to alleviate pressure or tension causing the positioning effect. See Hickey, C.; Gugino, L. D.; Aglio, L. S.; Mark, J. B.; Son, S. L. & Maddi, R., "Intraoperative somatosensory evoked potential monitoring predicts peripheral nerve injury during cardiac surgery," *Anesthesiology*, 78(1), pages 29-35, published 1992; Kamel, I. R.; Drum, E. T.; Koch, S. A.; Whitten, J. A.; Gaughan, J. P.; Barnette, R. E. & Wendling, W. W., "The use of somatosensory evoked potentials to determine the relationship between patient positioning and impending upper extremity nerve injury during spine surgery: a retrospective analysis," *Anesthesia & Analgesia*, 102(5), pages 1538-1542, published 2006; and Labrom, R. D.; Hoskins, M.; Reilly, C. W.; Tredwell, S. J. & Wong, P. K. H., "Clinical usefulness of somatosensory evoked potentials for detection of brachial plexopathy secondary to malpositioning in scoliosis surgery," *Spine*, 30(18), pages 2089-2093, published 2005.

However the IONM procedure is not automated, not available everywhere, is expensive, and is not traditionally performed for many types of surgery that give rise to positioning effect. In addition, IONM is not practical for use anywhere outside the operating room where unresponsive, weak or confined patients may incur positioning effect. Such monitoring may generally require highly trained technologists under physician supervision with sophisticated multichannel amplifier and display equipment. Unfortunately, such personnel and equipment are limited in availability, require pre-booking, and are costly. In addition, such monitoring is not traditionally done in many of the surgeries in which positioning effect occurs and is not traditionally done outside of the operating room where patients may remain at risk.

An algorithm for neurophysiology monitoring capable of quickly finding stimulation thresholds over multiple channels of a neurophysiology monitoring system is described in U.S. Patent Application No. 20080167574, to Farquhar, entitled "Multi-Channel Stimulation Threshold Detection Algorithm For Use In Neurophysiology Monitoring," filed Sep. 22, 2006, published Jul. 10, 2008, the contents of which are incorporated herein by reference in their entirety. However, the publication focuses on the use of an algorithm to determine stimulation thresholds for evoking neuromuscular responses and does not address positioning effect.

In an exemplary embodiment, a system, method, device and/or computer program product for automatically detecting positioning effect may be used to, e.g., but not limited to, detect, alert and/or ameliorate, etc., positioning effect during any surgery or situation where a patient is at risk, such as, e.g., but not limited to, an unconscious patient, a confined patient, an enfeebled patient, an anesthetized patient, etc.

FIG. 1 depicts an exemplary diagram of a system according to an exemplary embodiment of the present invention. According to an exemplary embodiment, the system 100, which may be coupled to a patient 101, may include, e.g., but not limited to, one or more recording electrodes 102, one or more stimulating electrodes 103, a positioning effect detection device (PEDD) 104, a table integration unit 105, an alert and display (or other output) unit 106, and a table 107. In an exemplary embodiment, the table 107 may include, e.g., but not limited to, any surface upon which the patient 101 may be placed, a bed, a chair, an operating room table, a pre-op table, and/or a post-op table, etc.

According to an exemplary embodiment, the recording electrodes 102 may be coupled to the head, neck, arms, legs, trunk, Erb's point and/or torso of the patient 101, and stimulating electrodes 103 may be coupled to the arms and/or legs of the patient 101.

According to an exemplary embodiment, the PEDD 104 may be electronically coupled to recording electrodes 102 and stimulating electrodes 103. In an exemplary embodiment, the PEDD 104 may be part of, may be coupled to, and/or may include, a computer. According to an exemplary embodiment, the PEDD 104 may include a computer, such as, e.g., but not limited to, the computer set forth in and described further below with reference to FIG. 2. In an exemplary embodiment, PEDD 104 may be electrically, electronically, and/or mechanically coupled to the table integration unit 105 and/or the alert and display unit 106.

According to an exemplary embodiment, the table integration unit 105 may be mechanically and/or electronically coupled to the table 107 and/or PEDD 104. In an exemplary embodiment, the table integration unit 105 may be incorporated in the table 107 and/or PEDD 104.

According to an exemplary embodiment, the alert and display unit 106 may be any of various well known output devices. In an exemplary embodiment, the alert and display unit 106 may be mechanically and/or electrically coupled to the PEDD 104 and/or table 107. According to an exemplary embodiment, the alert and display unit 106 may be incorporated in the table 107 and/or PEDD 104.

In an exemplary embodiment, the PEDD 104 may detect positioning effect in a patient 101 lying on the table 107 using the stimulating electrodes 103 and the recording electrodes 102. According to an exemplary embodiment, the PEDD 104 may communicate positioning effect information using the alert and display unit 106 to, e.g., operating room personnel.

In one exemplary embodiment, the PEDD 104 may further, correct positioning effect using a table integration unit 105 providing for movement of the table 107 to correct positioning effect.

According to an exemplary embodiment, the PEDD 104 may stimulate sensory or mixed nerves of the patient using the stimulating electrodes 103 to produce SEPs. In an exemplary embodiment, a PEDD 104 may be attached, coupled and/or connected to the patient 101 with stimulating electrodes 103, e.g., near the arms or legs over peripheral nervous structures, such as, but not limited to, e.g., the ulnar nerves, median nerves and posterior tibial nerves.

According to an exemplary embodiment, the PEDD 104 may use the recording electrodes 102 to detect SEPs generated by a patient's nervous system in response to the stimulation from the stimulating electrodes 103. In an exemplary embodiment, recording electrodes 102 may be attached, connected, and/or coupled over the spine, neck, and/or head.

According to an exemplary embodiment, based on the observed SEPs, the PEDD 104 may identify potential positioning effect injuries caused by positioning of the patient 101. In an exemplary embodiment, the PEDD 104 may detect changes in the SEPs, such as, e.g., but not limited to, changes in latency, changes in amplitude or changes in morphology. According to an exemplary embodiment, changes, such as, e.g., but not limited to, reductions or aberrations in the SEPs may indicate a positioning effect. In an exemplary embodiment, the PEDD 104 may identify a particular nerve structure affected by positioning effect based on the SEPs. The PEDD 104 may further recommend actions to ameliorate the positioning effect by recommending changes in position. In one exemplary embodiment, the PEDD 104 may move the patient automatically so as to prevent positioning effect injury to the patient 101.

In an exemplary embodiment, the stimulating electrode 103 may be incorporated into the PEDD 104, coupled to the PEDD 104, or attachable or connectable, directly or indirectly to the PEDD 104. According to an exemplary embodiment, the PEDD 104 may sequentially stimulate peripheral nerves via the stimulating electrode 103 while recording the SEPs via the recording electrode 102. According to an exemplary embodiment, the PEDD 104 may include an output operable to couple to the stimulating electrodes 103. In an exemplary embodiment, the recording electrodes 102 may be at least one of, incorporated into the PEDD 104, coupled to the PEDD 104, or attachable or connectable, directly or indirectly to the PEDD 104. According to an exemplary embodiment, the PEDD 104 may include an input operable to couple the PEDD 104 to the recording electrode 102. In an exemplary embodiment, the PEDD 104 may include a processor, a memory, a storage device or a computer.

In an exemplary embodiment, the SEPs may be returned to the PEDD 104 as electrical signals recorded by the recording electrodes 102. In an exemplary embodiment, the PEDD 104 may include standard industry components, such as, e.g., but not limited to, electric stimulators, pre-amplifiers, amplifiers and/or computer components, etc., to control stimulation and process return signals. According to an exemplary embodiment, the response to several stimuli may be averaged together to reduce noise and produce a clean signal. In an exemplary embodiment, proprietary or third party software may be used in signal processing to improve the signal-to-noise ratio and reduce the number of stimuli required to obtain a clean signal.

According to an exemplary embodiment, proprietary software may also be used to compare signals between limbs of a patient 101 to eliminate alerts from changes in signals due to systemic effects of anesthesia or blood pressure changes. In an exemplary embodiment, the PEDD 104 may obtain anesthesia information from an anesthesia machine and may calculate if changes in signals are due to anesthesia. According to an exemplary embodiment, the PEDD 104 may obtain blood pressure information from a blood pressure machine and may calculate if changes in signals are due to changes in a patient's sensed blood pressure.

In an exemplary embodiment, the alert and display unit 106 may include a display which may display various information, such as, e.g., but not limited to, areas being stimulated and recorded from, baseline and current signal traces, trends in signals, relevant changes in signals, location of signal changes, quality of recorded signals, position of electrodes, position of the table 107 or other similar device, location of table parts associated with body position, alerts due to significant changes in signals, and proposed or impending movements in the table 107 or similar device to mitigate the monitoring signal changes. In addition, the alert and display unit 106 may include, e.g., but not limited to, multiple buttons or control inputs. According to an exemplary embodiment, the buttons or inputs may allow an operator to set up the initial monitoring layout and interact with the alert and display unit 106 during monitoring to add additional information or respond to alerts. In an exemplary embodiment, the alert and display unit 106 may allow override of a change in signal by, e.g., but not limited to, an anesthesiologist, or other medical personnel, etc., when a signal change is related to a change in dose of anesthetic agent or some other event unrelated to positioning effect.

According to an exemplary embodiment, the PEDD 104 may include an interface operable to transfer information between the table integration unit 105 and the table 107. In an exemplary embodiment, the table integration unit 105 may pass information to and from the table 107 regarding the signals and positions of parts of the table. In an exemplary embodiment, the table integration module 105 may send signals to the table 107 instructing the table 107 to move in response to changes in SEPs in order to mitigate positioning effect.

According to an exemplary embodiment, the table integration unit 105 may obtain information from the table 107 about the position of the table's various parts, and any of the table's parts associated with the position of the patient's limbs. In an exemplary embodiment, the table integration unit 105 may update information in real time. In an exemplary embodiment, the PEDD 104 may receive the table position information and determine how to alleviate positioning effect based on the table position information. According to an exemplary embodiment, the table integration unit 105 may transfer information regarding a potential positioning effect injury and may cause the table 107 to change in position to alleviate the potential injury.

In an exemplary embodiment, the table integration module 105 may send signals to the table 107 instructing the table 107 to move in response to changes in signals in order to mitigate positioning effect. According to an exemplary embodiment, the table 107 may move based on instructions from a table integration module 105. In an exemplary embodiment, the table 107 may include servo-mechanism controlled parts, and/or other electro-mechanical moving parts, and may position parts of the table 107 using the electro-mechanisms. According to an exemplary embodiment, the PEDD 104 may be integrated into a table 107. In an exemplary embodiment, the table integration unit 105 may be left out when using tables 107 that do not have sufficient moving parts or automated moving parts.

According to an exemplary embodiment, the PEDD 104 and table 107 may cooperatively move the patient 101 so as to prevent positioning effect injuries. In an exemplary embodiment, the PEDD 104 may identify a potential positioning effect injury. According to an exemplary embodiment, the table 107 may then move the patient 101 so as to avoid potential injury. In an exemplary embodiment, the PEDD 104 may then determine if the positioning effect has been reduced. According to an exemplary embodiment, if the positioning effect has been reduced, the table 107 may reposition the patient further so that the positioning effect is eliminated. In an exemplary embodiment, if the positioning effect has not been reduced, the table 107 may reposition the patient differently. According to an exemplary embodiment, if the positioning effect is worsened, the table 107 may reposition the patient back to the patient's original position. In an exemplary embodiment, the table 107 may include, e.g., but is not limited to, any surface upon which the patient 101 may be placed, a bed, a chair, an operating room table, a pre-operation table, and/or a post-operation table.

In an exemplary embodiment, the table integration unit 105 and/or the alert or the display unit 106 may be subcomponent modules of the PEDD 104 or may be coupled to the PEDD 104. According to an exemplary embodiment, an override functionality may be another subcomponent module of the PEDD 104. Override functionality may include interaction with the PEDD 104 at any time by several methods including tactile or voice command.

Exemplary Processing and Communications Embodiments

Figure 2:
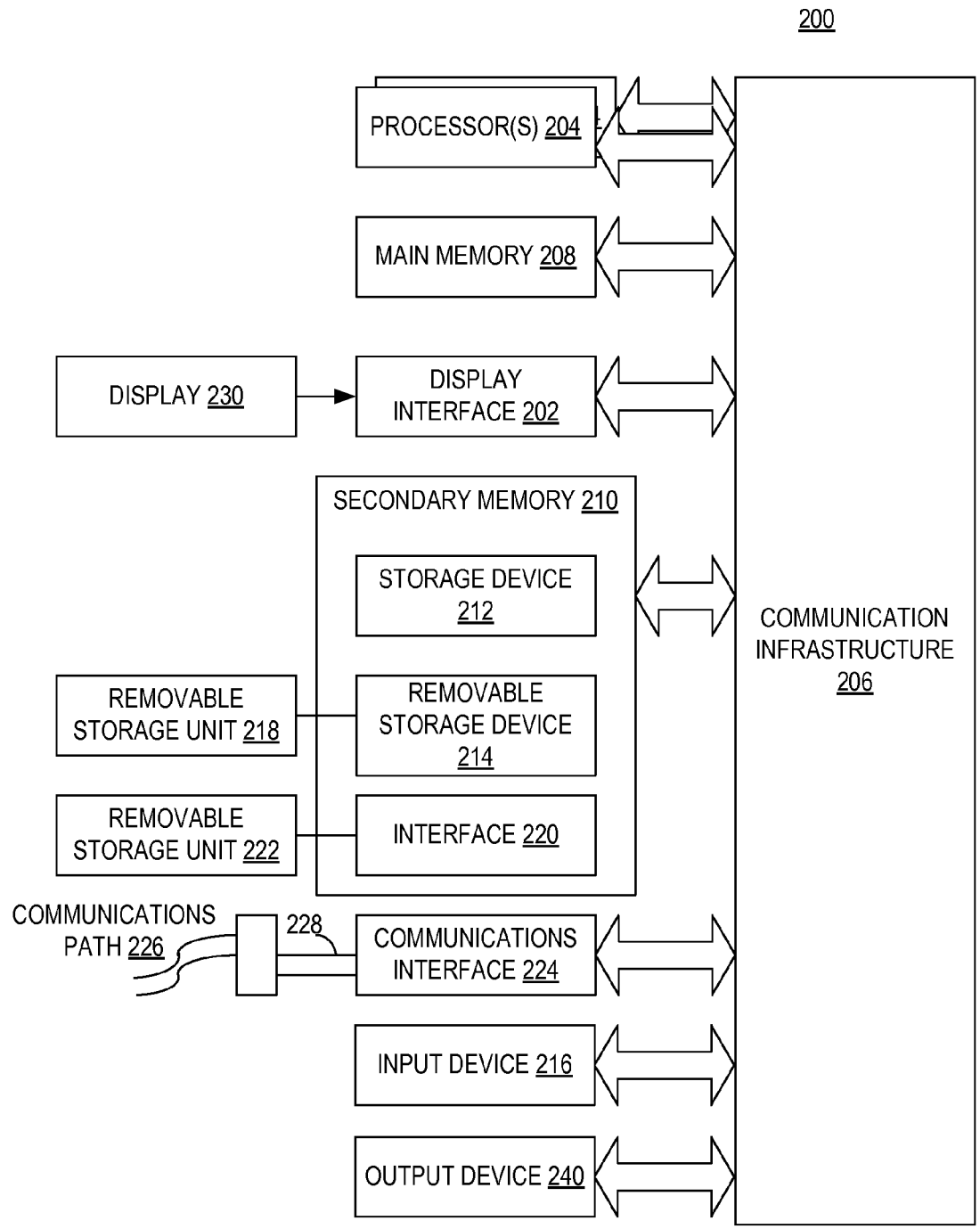
FIG. 2 depicts an exemplary embodiment of a computer system that may be used in association with, in connection with, and/or in place of, but not limited to, any of the foregoing components and/or systems.

FIG. 2 depicts an exemplary embodiment of a computer system 200 that may be used in association with, in connection with, and/or in place of, e.g., but not limited to, any of the foregoing components and/or systems.

The present embodiments (or any part(s) or function(s) thereof) may be implemented using hardware, software, firmware, or a combination thereof and may be implemented in one or more computer systems or other processing systems. In fact, in one exemplary embodiment, the invention may be directed toward one or more computer systems capable of carrying out the functionality described herein. An example of a computer system 200 is shown in FIG. 2, depicting an exemplary embodiment of a block diagram of an exemplary computer system useful for implementing the present invention. Specifically, FIG. 2 illustrates an example computer 200, which in an exemplary embodiment may be, e.g., (but not limited to) a personal computer (PC) system running an operating system such as, e.g., (but not limited to) WINDOWS MOBILE™ for POCKET PC, or MICROSOFT® WINDOWS® NT/98/2000/XP/CE/7/VISTA, etc. available from MICROSOFT® Corporation of Redmond, Wash., U.S.A., SOLARIS® from SUN® Microsystems of Santa Clara, Calif., U.S.A., OS/2 from IBM® Corporation of Armonk, N.Y., U.S.A., Mac/OS from APPLE® Corporation of Cupertino, Calif., U.S.A., etc., or any of various versions of UNIX® (a trademark of the Open Group of San Francisco, Calif., USA) including, e.g., LINUX®, HPUX®, IBM AIX®, and SCO/UNIX®, etc. However, the invention may not be limited to these platforms. Instead, the invention may be implemented on any appropriate computer system running any appropriate operating system. In one exemplary embodiment, the present invention may be implemented on a computer system operating as discussed herein. An exemplary computer system, computer 200 is shown in FIG. 2. Other components of the invention, such as, e.g., (but not limited to) a computing device, a communications device, a telephone, a personal digital assistant (PDA), a personal computer (PC), a handheld PC, client workstations, thin clients, thick clients, proxy servers, network communication servers, remote access devices, client computers, server computers, routers, web servers, data, media, audio, video, telephony or streaming technology servers, etc., may also be implemented using a computer such as that shown in FIG. 2.

The computer system 200 may include one or more processors, such as, e.g., but not limited to, processor(s) 204. The processor(s) 204 may be connected to a communication infrastructure 206 (e.g., but not limited to, a communications bus, cross-over bar, or network, etc.). Various exemplary software embodiments may be described in terms of this exemplary computer system. After reading this description, it will become apparent to a person skilled in the relevant art(s) how to implement the invention using other computer systems and/or architectures.

Computer system 200 may include a display interface 202 that may forward, e.g., but not limited to, graphics, text, and other data, etc., from the communication infrastructure 206 (or from a frame buffer, etc., not shown) for display on the display unit 230.

The computer system 200 may also include, e.g., but may not be limited to, a main memory 208, random access memory (RAM), and a secondary memory 210, etc. The secondary memory 210 may include, for example, (but may not be limited to) a hard disk drive 212 and/or a removable storage drive 214, representing a floppy diskette drive, a magnetic tape drive, an optical disk drive, a magneto-optical disk drive, a compact disk drive CD-ROM, a digital versatile disk (DVD), a write once read many (WORM) device, a flash memory device, etc. The removable storage drive 214 may, e.g., but not limited to, read from and/or write to a removable storage unit 218 in a well known manner. Removable storage unit 218, also called a program storage device or a computer program product, may represent, e.g., but not limited to, a floppy disk, a magnetic tape, an optical disk, a magneto-optical disk, a compact disk, a flash memory device, etc. which may be read from and written to by removable storage drive 214. As will be appreciated, the removable storage unit 218 may include a computer usable storage medium having stored therein computer software and/or data.

In alternative exemplary embodiments, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 222 and interfaces 220, which may allow software and data to be transferred from the removable storage unit 222 to computer system 200.

Computer 200 may also include an input device 216 such as, e.g., (but not limited to) a mouse or other pointing device such as a digitizer, and a keyboard or other data entry device (none of which are labeled).

Computer 200 may also include output devices 240, such as, e.g., (but not limited to) display 230, and display interface 202. Computer 200 may include input/output (I/O) devices such as, e.g., (but not limited to) communications interface 224, cable 228 and communications path 226, etc. These devices may include, e.g., but not limited to, a network interface card, and modems (neither are labeled). Communications interface 224 may allow software and data to be transferred between computer system 200 and external devices. Examples of communications interface 224 may include, e.g., but may not be limited to, a modem, a network interface (such as, e.g., an Ethernet card), a communications port, a Personal Computer Memory Card International Association (PCMCIA) slot and card, etc. Software and data transferred via communications interface 224 may be in the form of signals 228 which may be electronic, electromagnetic, optical or other signals capable of being received by communications interface 224. These signals 228 may be provided to communications interface 224 via, e.g., but not limited to, a communications path 226 (e.g., but not limited to, a channel). This channel 226 may carry signals 228, which may include, e.g., but not limited to, propagated signals, and may be implemented using, e.g., but not limited to, wire or cable, fiber optics, a telephone line, a cellular link, an radio frequency (RF) link and other communications channels, etc.

In this document, the terms "computer program medium" and "computer readable medium" may be used to generally refer to media such as, e.g., but not limited to removable storage drive 214, a hard disk installed in hard disk drive and/or other storage device 212, and signals 228, etc. These computer program products may provide software to computer system 200. The invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses and/or devices for performing the operations herein. An apparatus may be specially constructed for the desired purposes, or it may comprise a general purpose device selectively activated or reconfigured by a program stored in the device.

Embodiments of the invention may be implemented in one or a combination of hardware, firmware, and software. Embodiments of the invention may also be implemented as instructions stored on a machine-readable medium, which may be read and executed by a computing platform to perform the operations described herein. A machine-readable medium may include any mechanism for storing or transmitting information in a form readable by a machine (e.g., a computer). For example, an exemplary machine-readable storage medium may include, e.g., but not limited to, read only memory (ROM); random access memory (RAM); magnetic disk storage media; optical storage media; magneto-optical storage media; flash memory devices; other exemplary storage devices capable of storing electrical, optical, acoustical or other form of propagated signals (e.g., carrier waves, infrared signals, digital signals, etc.) thereon, and others.

Computer programs (also called computer control logic), may include object oriented computer programs, and may be stored in main memory 208 and/or the secondary memory 210 and/or removable storage units 214, also called computer program products. Such computer programs, when executed, may enable the computer system 200 to perform the features of the present invention as discussed herein. In particular, the computer programs, when executed, may enable the processor or processors 204 to provide a method to control and/or manage operation of a positioning effect detection device according to an exemplary embodiment of the present invention. Accordingly, such computer programs may represent controllers of the computer system 200.

In another exemplary embodiment, the invention may be directed to a computer program product comprising a computer readable medium having control logic (computer software) stored therein. The control logic, when executed by the processor 204, may cause the processor 204 to perform the functions of the invention as described herein. In another exemplary embodiment where the invention may be implemented using software, the software may be stored in a computer program product and loaded into computer system 200 using, e.g., but not limited to, removable storage drive 214, hard drive 212 or communications interface 224, etc. The control logic (software), when executed by the processor 204, may cause the processor 204 to perform the functions of the invention as described herein. The computer software may run as a standalone software application program running atop an operating system, or may be integrated into the operating system.

In yet another embodiment, the invention may be implemented primarily in hardware using, for example, but not limited to, hardware components such as application specific integrated circuits (ASICs), or one or more state machines, etc. Implementation of the hardware state machine so as to perform the functions described herein will be apparent to persons skilled in the relevant art(s).

In another exemplary embodiment, the invention may be implemented primarily in firmware.

In yet another exemplary embodiment, the invention may be implemented using a combination of any of, e.g., but not limited to, hardware, firmware, and software, etc.

Exemplary embodiments of the invention may also be implemented as instructions stored on a machine-readable or accessible storage medium, which may be read and executed by a computing platform to perform the operations described herein. A machine-readable storage medium may include any mechanism for storing or transmitting information in a form readable by a machine (e.g., a computer). For example, a machine-readable medium may include, e.g., but not limited to, read only memory (ROM); random access memory (RAM); magnetic disk storage media; optical storage media; magneto-optical storage media; flash memory devices; other exemplary storage devices capable of storing electrical, optical, acoustical or other form of propagated signals (e.g., carrier waves, infrared signals, digital signals, etc.) thereon, and others.

The exemplary embodiment of the present invention makes reference to, e.g., but not limited to, communications links, wired, and/or wireless networks. Wired networks may include any of a wide variety of well known means for coupling voice and data communications devices together. A brief discussion of various exemplary wireless network technologies that may be used to implement the embodiments of the present invention now are discussed. The examples are non-limiting. Exemplary wireless network types may include, e.g., but not limited to, code division multiple access (CDMA), spread spectrum wireless, orthogonal frequency division multiplexing (OFDM), 1G, 2G, 3G wireless, Bluetooth, Infrared Data Association (IrDA), shared wireless access protocol (SWAP), "wireless fidelity" (Wi-Fi), WIMAX, and other IEEE standard 802.11-compliant wireless local area network (LAN), 802.16-compliant wide area network (WAN), and ultrawideband (UWB) networks, etc.

Bluetooth is an emerging wireless technology promising to unify several wireless technologies for use in low power radio frequency (RF) networks.

IrDA is a standard method for devices to communicate using infrared light pulses, as promulgated by the Infrared Data Association from which the standard gets its name. Since IrDA devices use infrared light, they may depend on being in line of sight with each other.

The exemplary embodiments of the present invention may make reference to WLANs. Examples of a WLAN may include a shared wireless access protocol (SWAP) developed by Home radio frequency (HomeRF), and wireless fidelity (Wi-Fi), a derivative of IEEE 802.11, advocated by the wireless Ethernet compatibility alliance (WECA). The IEEE 802.11 wireless LAN standard refers to various technologies that adhere to one or more of various wireless LAN standards. An IEEE 802.11 compliant wireless LAN may comply with any of one or more of the various IEEE 802.11 wireless LAN standards including, e.g., but not limited to, wireless LANs compliant with IEEE std. 802.11a, b, d or g, such as, e.g., but not limited to, IEEE std. 802.11 a, b, d and g, (including, e.g., but not limited to IEEE 802.11g-2003, etc.), etc.

Unless specifically stated otherwise, as apparent from the following discussions, it may be appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

According to an exemplary embodiment, exemplary methods set forth herein may be performed by an exemplary one or more computer processor(s) adapted to process program logic, which may be embodied on an exemplary computer accessible storage medium, which when such program logic is executed on the exemplary one or more processor(s) may perform such exemplary steps as set forth in the exemplary methods.

Exemplary Operating Room Table Embodiment

Figure 3:
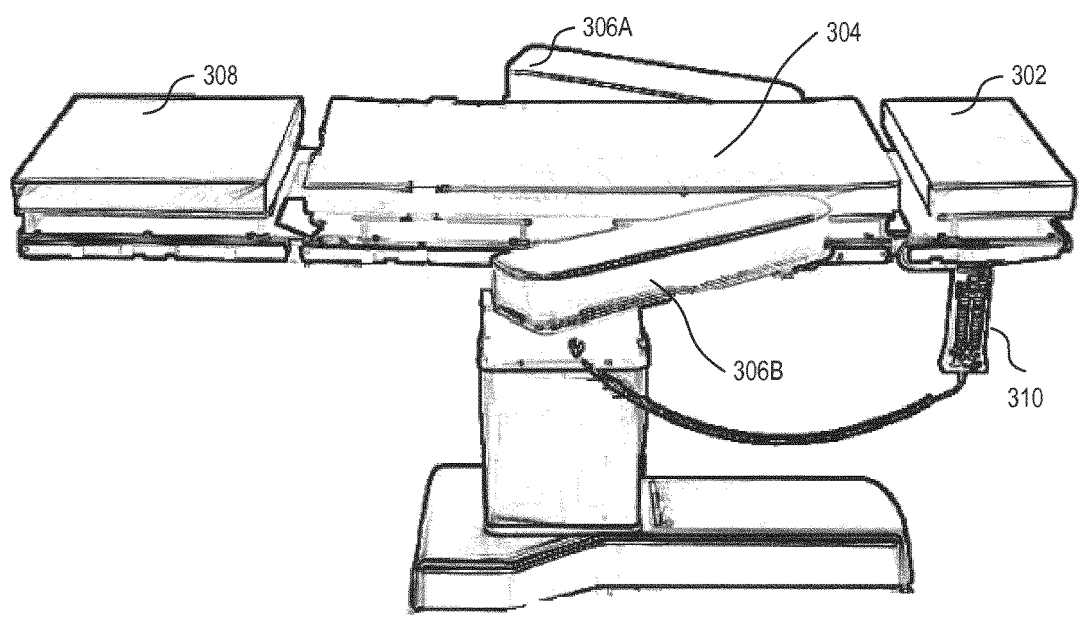
FIG. 3 depicts an exemplary diagram of the table, according to an exemplary embodiment of the present invention.

FIG. 3 depicts an exemplary diagram of the table 107, according to an exemplary embodiment of the present invention. According to an exemplary embodiment, the table 107 may include parts operable to move the patient. In an exemplary embodiment, the table 107 may include, e.g., but not limited to, a head piece 302, a torso piece 304, one or more arm pieces 306A, 306B, and a leg piece 308. According to an exemplary embodiment, the table 107 may use parts of the table to move body parts of a patient, such as, e.g., but not limited to, the patient's head, the patient's arms, the patient's legs, etc., individually or in combination. In an exemplary embodiment, the table 107 may position a patient, such as, e.g., but not limited to, tilt, rotate, flex, reflex, incline, decline, etc. According to an exemplary embodiment, the table 107 may include an interface 310 operable to receive instructions from a user to position the table 107. According to one exemplary embodiment, the interface 310 may be coupled to the table, as shown, via an exemplary cable. According to another exemplary embodiment, the interface 310 may be coupled via, e.g., but not limited to a communications link such as, e.g., but not limited to, a wireless communications link, etc. In an exemplary embodiment, the table 107 may receive information and/or instructions for positioning from the table integration unit 105. According to an exemplary embodiment, the table 107 may receive information from a user and/or a table integration unit 105. According to an exemplary embodiment, components may be attached to and/or detached from the table 107 to facilitate particular types of operations. An exemplary table 107 may be an AMSCO 3085 SP Surgical Table made by Steris Corporation of Mentor, Ohio, U.S.A.

Exemplary Electromechanical Control

According to an exemplary embodiment of the present invention, the table 107 may move one or more portions of the table 107 using, e.g., but not limited to, electromechanical movement. In an exemplary embodiment, electromechanical movement may include, e.g., but not limited to, hydraulic movement, pneumatic movement, magnetic movement, or mechanical movement. According to an exemplary embodiment, the table 107 may include, e.g., but not limited to, pumps. In an exemplary embodiment, the exemplary pumps may manipulate fluid and/or gas pressure to move parts of the table 107. According to an exemplary embodiment, the table may include, e.g., but not limited to, electrical motors. In an exemplary embodiment, the exemplary electrical motors may provide mechanical force to move parts of the table 107.

According to an exemplary embodiment, the table 107 may include one or more servo-mechanisms. In an exemplary embodiment, the servo-mechanism may automatically ameliorate positioning effect. According to an exemplary embodiment, the servo-mechanism may include, e.g., but not limited to, electro-mechanical parts of the table 107, where the parts of the table may be moved in response to feedback based on positioning effect. In an exemplary embodiment, the servo-mechanism may be, e.g., but not limited to, a servo-motor. According to an exemplary embodiment, one or more parts of the table 107 may be electromechanically positioned by the exemplary servo-motor to reduce positioning effect.

Exemplary Patient Module

In an exemplary embodiment, the PEDD 104 may be a small, lightweight PDA-sized device that may hang on, e.g., but not limited to, an operating table 107. The PEDD 104 may have storage and/or print features to provide a graphical record of the results. The PEDD 104 may be connected and/or coupled to a display 106 through, e.g., but not limited to, a single cable. According to one exemplary embodiment, the display 106 may include, one, two, or more screens. The first exemplary screen may display an anatomical diagram that may first light up in, e.g., but not limited to, yellow to warn of a significant change and then, e.g., but not limited to, in red as an alarm of a critical change in the waveforms. The first exemplary screen may be designed so interpretation of data may not require expertise in neuromonitoring. The second exemplary screen may display the waveforms and the waveform's associated amplitude and latency values.

In an exemplary embodiment, the PEDD 104 may be packaged as a lightweight 5"×3"×1" plastic, liquid proof case. The PEDD 104 may have 4-stimulation channels and 6 channels for recording, according to an exemplary embodiment. The electrodes may connect and/or couple to the PEDD patient module (PEDD-PM) through, e.g., but not limited to, a single D-shell connector that may be attached and/or coupled to exemplary, but non-limiting, disposable electrodes. In an exemplary embodiment, each electrode may be color-coded and/or labeled, indicating placement sites (including, e.g., but not limited to, Stim-R Wrist, Record-L Cortical, etc.). The electrodes may be surface-sticky, in an exemplary embodiment. However the electrodes, such as, e.g., but not limited to, two scalp electrodes, may instead be sub-dermal needles. In one exemplary embodiment, the display 106 may be, e.g., but not limited to, a small flat panel that may fit among other physiological monitoring displays. The exemplary flat panel display may plug into an electrical, such as, e.g., but not limited to, AC or DC, receptacle for power.

According to an exemplary embodiment, the PEDD 104 may be easy to use. An anesthesiologist and/or surgical nurse may be able to connect and/or couple all of the electrodes 102 and 103 in, e.g., but not limited to, about two minutes or less. In an exemplary embodiment, the PEDD 104 may automatically test for electrode impedances and provide information on the quality of the recording. According to an exemplary embodiment, the PEDD 104 may automatically adjust the stimulation level. In an exemplary embodiment, the PEDD 104, if desired, may provide an alarm if the potentials deviate significantly from baseline measurements. According to an exemplary embodiment, the PEDD 104 may also provide an alert if the patient has, e.g., but not limited to, a peripheral neuropathy or other nerve disorder that may prevent the collection of reliable baseline waveforms.

Embodiments of the present invention may include apparatuses for performing the operations herein. An apparatus may be specially constructed for the desired purposes, or it may comprise a general purpose device selectively activated or reconfigured by a program stored in the device. In yet another exemplary embodiment, the invention may be implemented using a combination of any of, for example, but not limited to, hardware, firmware and software, etc. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

In the description and claims, the terms "coupled" and "connected," along with their derivatives, may be used. It should be understood that these terms are not intended as synonyms for each other. Rather, in particular embodiments, "connected" may be used to indicate that two or more elements are, or may be, in direct physical or electrical contact with each other. "Coupled" may mean that two or more elements are, or may be, in direct physical or electrical contact. However, "coupled" may also mean that two or more elements are not in direct contact with each other, but yet may still co-operate or interact with each other.

Finally, while various exemplary embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

What is claimed is:

1. A method of identifying positioning effect in a patient, the method comprising:
   stimulating one or more peripheral nerve structures with one or more electrical pulses from a stimulating electrode;
   recording resultant electrical waveforms generated by a nervous system of the patient in response to the electrical pulses using a recording electrode;
   detecting, by a computing device, a change in the resultant electrical waveforms;
   analyzing, by the computing device, the detected change in the resultant electrical waveforms to automatically identify the positioning effect, the positioning effect comprising an immediate or potential injury to the one or more peripheral nerve structures due to stress associated with a position in which the patient has been placed for medical care or treatment; and
   forwarding data to a display, the data comprising information for displaying an anatomical diagram that depicts a location of the detected change.

2. The method of claim 1, wherein said at least one stimulating electrode is coupled to at least one of:
- an arm of the patient;
- a leg of the patient;
- an ulnar nerve of the patient;
- a median nerve of the patient; or
- a posterior tibial nerve of the patient.

3. The method of claim 1, wherein said at least one recording electrode is coupled to at least one of:
- a trunk of the patient;
- an Erb's point of the patient;
- a head of the patient; or
- a neck of the patient.

4. The method of claim 1, wherein the peripheral nerve structure comprises one or more of the group consisting of: a peripheral nerve, a nerve root, a nerve trunk, a nerve plexus, a cord, and a division.

5. The method of claim 1, wherein the resultant electrical waveforms are somatosensory evoked potential waveforms.

6. The method of claim 1, wherein the change in the resultant electrical waveforms comprises a change in a latency, an amplitude, or a morphology of the resultant electrical waveforms.

7. The method of claim 1, wherein analyzing the detected change comprises at least one of:
- comparing, by the computing device, information based on the resultant electrical waveforms to information from an anesthesia machine to determine when changes in the resultant electrical waveforms are due to anesthesia; or
- comparing, by the computing device, information based on the resultant electrical waveforms to information from a blood pressure machine to determine when changes in the resultant electrical waveforms are due to blood pressure.

8. The method of claim 1, further comprising: determining how to reduce the positioning effect based on a position of a table.

9. The method of claim 1, further comprising: providing information based on the positioning effect to a table.

10. The method of claim 9, further comprising:
providing information to the table to at least partially reposition the table to reduce the positioning effect.

11. The method of claim 1, further comprising:
adjusting a position of the patient based on the positioning effect using an electro-mechanism of a table.

12. The method of claim 1, further comprising:
alerting a user to the positioning effect using at least one of:
- a notification;
- an alert;
- a communication;
- an indication; or
- an alarm.

13. The method of claim 1, further comprising:
displaying the information based on the resultant electrical waveforms on the display.

14. The method of claim 1, further comprising: receiving a user input regarding an accuracy of the resultant electrical waveforms.

15. The method of claim 1, wherein analyzing the detected change comprises averaging together the resultant electrical waveforms generated in response to several stimulations to reduce noise.

* * * * *